(12) United States Patent
Krause et al.

(10) Patent No.: US 7,715,906 B2
(45) Date of Patent: May 11, 2010

(54) METHOD AND APPARATUS FOR DETECTING NOISE IN AN IMPLANTABLE MEDICAL DEVICE

(75) Inventors: Paul G. Krause, Shoreview, MN (US); Karen J. Kleckner, New Brighton, MN (US); Steven N. Lu, Fridley, MN (US); David E. Ritscher, Minneapolis, MN (US); Cameron J. Kaszas, Minneapolis, MN (US); Michael T. Hemming, Kiowa, CO (US)

(73) Assignee: Medtronic, Inc., Minneapolis, MN (US)

( * ) Notice: Subject to any disclaimer, the term of this patent is extended or adjusted under 35 U.S.C. 154(b) by 420 days.

(21) Appl. No.: 11/757,628

(22) Filed: Jun. 4, 2007

(65) Prior Publication Data

US 2008/0300497 A1 Dec. 4, 2008

(51) Int. Cl.
A61B 5/04 (2006.01)
(52) U.S. Cl. .................. 600/515; 600/508; 600/509
(58) Field of Classification Search .......... 600/508, 600/509, 515
See application file for complete search history.

(56) References Cited

U.S. PATENT DOCUMENTS

| | | | |
|---|---|---|---|
| 4,374,382 A | 2/1983 | Markowitz | |
| 4,556,063 A | 12/1985 | Thompson et al. | |
| 4,708,144 A | 11/1987 | Hamilton et al. | |
| 4,880,004 A | 11/1989 | Baker, Jr. et al. | |
| 4,903,699 A | 2/1990 | Baker, Jr. et al. | |
| 4,974,589 A | 12/1990 | Sholder | |
| 5,117,824 A | 6/1992 | Keimel et al. | |
| 5,127,404 A | 7/1992 | Wyborny et al. | |
| 5,163,427 A | 11/1992 | Keimel | |
| 5,188,105 A | 2/1993 | Keimel | |
| 5,193,535 A | 3/1993 | Bardy et al. | |
| 5,203,326 A * | 4/1993 | Collins | 607/4 |
| 5,269,300 A | 12/1993 | Kelly et al. | |
| 5,271,411 A * | 12/1993 | Ripley et al. | 600/515 |
| 5,339,820 A | 8/1994 | Henry et al. | |
| 5,354,316 A | 10/1994 | Keimel | |
| 5,476,485 A | 12/1995 | Weinberg et al. | |
| 5,545,186 A | 8/1996 | Olson et al. | |
| 5,683,432 A | 11/1997 | Goedeke et al. | |

(Continued)

FOREIGN PATENT DOCUMENTS

WO 2004023995 3/2004

(Continued)

OTHER PUBLICATIONS

International Search Report, PCT/US2008/065767, Oct. 23, 2008, 7 Pages.

*Primary Examiner*—Carl H Layno
*Assistant Examiner*—Yun Haeng Lee
(74) *Attorney, Agent, or Firm*—Michael C. Soldner

(57) ABSTRACT

An implantable medical device and associated method monitor a physiological signal for sensing physiological events and detecting a physiological condition in response to the sensed physiological events. The device senses a first event from the physiological signal, senses a noise signal in the physiological signal and senses a next event from the physiological signal wherein the first event and the next event define a signal interval. The signal interval is declared as a noisy interval in response to the sensed noise signal.

28 Claims, 11 Drawing Sheets

U.S. PATENT DOCUMENTS

| | | |
|---|---|---|
| 5,759,196 A | 6/1998 | Hess et al. |
| 5,855,593 A | 1/1999 | Olson et al. |
| 5,987,352 A | 11/1999 | Klein et al. |
| 6,112,119 A | 8/2000 | Schuelke et al. |
| 6,217,525 B1 | 4/2001 | Medema et al. |
| 6,236,882 B1 | 5/2001 | Lee et al. |
| 6,377,851 B1 | 4/2002 | Shieh et al. |
| 6,512,940 B1 | 1/2003 | Brabec et al. |
| 6,522,915 B1 | 2/2003 | Ceballos et al. |
| 6,599,250 B2 | 7/2003 | Webb et al. |
| 6,622,046 B2 | 9/2003 | Fraley et al. |
| 7,027,858 B2 | 4/2006 | Cao et al. |
| 7,031,765 B2 | 4/2006 | Ritscher et al. |
| 2001/0025137 A1 | 9/2001 | Webb et al. |
| 2003/0083716 A1 | 5/2003 | Nicolelis et al. |
| 2004/0106957 A1 | 6/2004 | Palreddy et al. |
| 2004/0260350 A1 | 12/2004 | Brandstetter et al. |
| 2005/0154421 A1 | 7/2005 | Ousdigian |

FOREIGN PATENT DOCUMENTS

| | | |
|---|---|---|
| WO | 2004093974 A | 11/2004 |

* cited by examiner

METHOD AND APPARATUS FOR DETECTING NOISE IN AN IMPLANTABLE MEDICAL DEVICE

FIELD OF THE INVENTION

The present invention generally relates to implantable medical devices (IMDs), and, more particularly, the present invention relates to detecting noisy physiologic data intervals.

BACKGROUND

Implantable medical devices (IMDs) sense physiological signals for diagnosing a patient condition and/or managing the delivery of a medical therapy. One example of an IMD used for monitoring a patient is an implantable loop recorder (ILR) that records a patient's ECG subcutaneously for diagnosing pathologic conditions like fainting or transient arrhythmias. A pair of sense electrodes spaced apart on the device housing are used to sense the subcutaneous ECG. The ILR records the ECG signal when the patient, feeling symptomatic, activates the recording function of the ILR by holding a telemetry-enabled activator over the ILR and pressing a button. Alternatively, the detection of an arrhythmia by the ILR using arrhythmia detection algorithms may automatically trigger ECG signal storage.

Another IMD that relies on subcutaneously sensed ECG signals is a subcutaneous implantable cardioverter defibrillator (SubQ ICD). The SubQ ICD detects arrhythmias using the subcutaneously sensed ECG and delivers cardioversion/defibrillation (CV/DF) therapy in response to detecting malignant tachcyardias.

Subcutaneous ECG sensing in such devices is complicated by the presence of non-cardiac myopotentials (e.g., skeletal muscle activations in the vicinity of the implanted device), motion artifact, other physiological signals (i.e., respiration and gastrointestinal signals), electromagnetic interference (typically 50 or 60 Hz electrical noise from power mains), and electrostatic discharge (ESD). ESD is characterized by a large common mode or differential mode transient that saturates the input amplifier or overflows the input to an analog-to-digital converter, preventing the detection of cardiac signals for a period of several seconds. Noise in the subcutaneous ECG signal can interfere with the appropriate detection and response to cardiac arrhythmias or other cardiac conditions by implantable devices such as an ILR or SubQ ICD. The presence of noise in the ECG signal sensed by an ILR may trigger data storage inappropriately, causing the memory to filled with data of little use in diagnosing the patient's condition. Over sensing of noise in the subcutaneous ECG signal by a SubQ ICD may cause inappropriate tachycardia detection and unnecessary delivery of a CV/DF high voltage shock.

DETAILED DESCRIPTION

Figure 1:
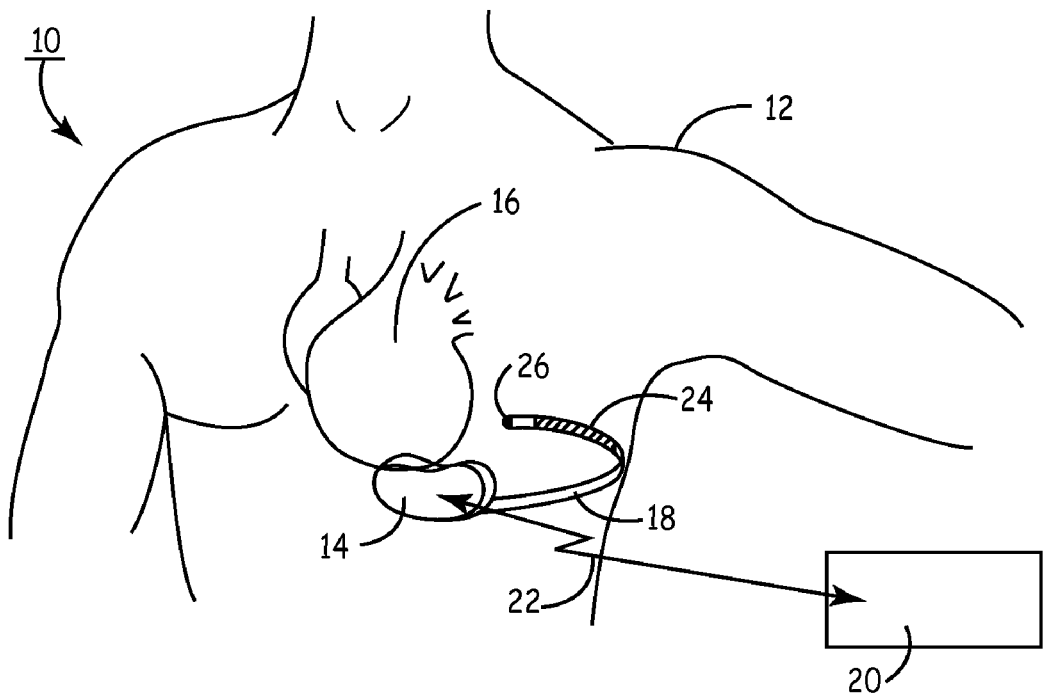
FIG. 1 depicts a SubQ ICD implanted in a patient.

In the following description, references are made to illustrative embodiments for carrying out the invention. It is understood that other embodiments may be utilized without departing from the scope of the invention. For purposes of clarity, the same reference numbers are used in the drawings to identify similar elements. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Examples of IMDs in which embodiments of the present invention may be implemented are described below in conjunction with FIGS. 1 through 5. A SubQ ICD is described in conjunction with FIGS. 1 through 3, and an ILR is described in conjunction with FIGS. 4 and 5. While these devices are representative of IMDs that rely on sensing physiological signals subject to noise contamination, embodiments of the present invention are not limited to these illustrative devices. Methods and apparatus described herein for sensing noise in a physiological signal, declaring a noisy physiological signal interval in response to detecting noise, and adjusting a response by the IMD to the physiological signal interval in response to declaring the interval noisy may be implemented in any IMD configured to sense physiological signals for detecting physiological events and provide a response thereto. Such IMDs include pacemakers, ICDs, neurostimulators, insertable cardiac monitors, drug delivery devices and the like.

FIG. 1 shows a SubQ ICD 10 implanted in a patient 12. SubQ ICD 10 includes a housing 14, which is generally shaped to promote ease of subcutaneous implant and minimize patient discomfort. SubQ ICD 10 is adapted to be implanted outside the ribcage of patient 12, anterior to the cardiac notch. A subcutaneous sensing and cardioversion/defibrillation therapy delivery lead 18 is electrically coupled to SubQ ICD 10 via a connector block (not shown). Lead 18 includes a high voltage coil electrode 24 and may include one or more distal sensing electrodes 26 for use in sensing subcutaneous ECG signals. Lead 18 is tunneled subcutaneously to a posterior location adjacent a portion of a latissimus dorsi muscle of patient 12. Specifically, lead 18 is tunneled subcutaneously or submuscularly from the median implant pocket of SubQ ICD 10 laterally and posterially to the patient's back to a location opposite the heart such that the heart 16 is disposed between the SubQ ICD 10 the electrodes 26 and 24.

Further referring to FIG. 1, an external device 20, which may be embodied as a home monitor or programmer is shown in telemetric communication with SubQ ICD 10 by wireless communication link 22, which may be, but not limited to, an RF communication link.

Figure 2:
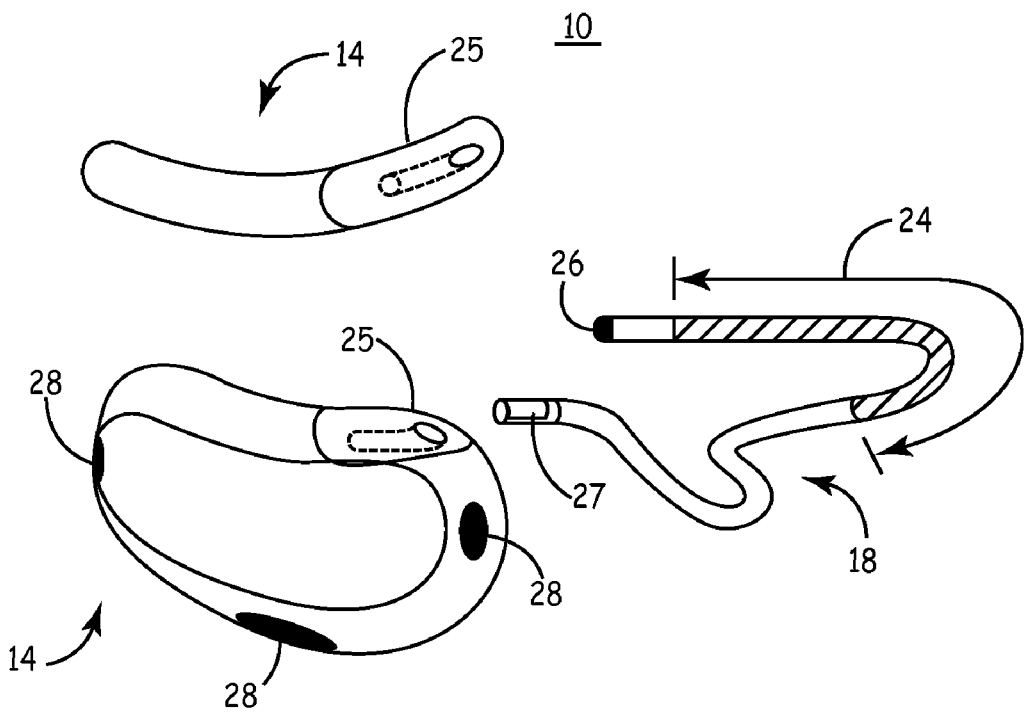
FIG. 2 depicts a frontal and side view of a SubQ ICD and an electrical lead associated therewith.

FIG. 2 is top and frontal views of SubQ ICD 10. SubQ ICD 10 includes housing 14 with a connector block 25 for attaching a subcutaneous sensing and cardioversion/defibrillation therapy delivery lead 18. SubQ ICD 10 may be constructed, for example, of stainless steel, titanium or ceramic.

Subcutaneous lead 18 includes of a distal defibrillation coil electrode 24, a distal sensing electrode 26, an insulated flexible lead body and a proximal connector pin 27 for connection to SubQ ICD circuitry enclosed within housing 14 via connector block 25. A subcutaneous electrode array (SEA) 28 is incorporated on housing 14, including three electrodes in the embodiment shown in FIG. 2.

Electrodes included in SEA 28 are welded into place on the flattened periphery of the SubQ ICD housing 14 and are connected via wires (not shown in FIG. 2) to electronic circuitry (described herein below) inside housing 14. SEA 28 may be constructed of flat plates, or alternatively, spiral electrodes as described in U.S. Pat. No. 6,512,940 "Subcutaneous Spiral Electrode for Sensing Electrical Signals of the Heart" to Brabec, et al and mounted in a non-conductive surround shroud as described in U.S. Pat. No. 6,522,915 "Surround Shroud Connector and Electrode Housings for a Subcutaneous Electrode Array and Leadless ECGs" to Ceballos, et al and U.S. Pat. No. 6,622,046 "Subcutaneous Sensing Feedthrough/Electrode Assembly" to Fraley, et al, all incorporated herein by reference in their entireties.

ECG sensing vectors may be selected using any of the electrodes included in SEA 28 and lead-based sensing electrode 26. Such subcutaneous sensing vectors may be subjected to considerable non-cardiac noise which can interfere with accurate arrhythmia detection. As will be described herein, methods for detecting noisy cardiac depolarization intervals can be used to prevent inappropriate detection of arrhythmias.

Figure 3:
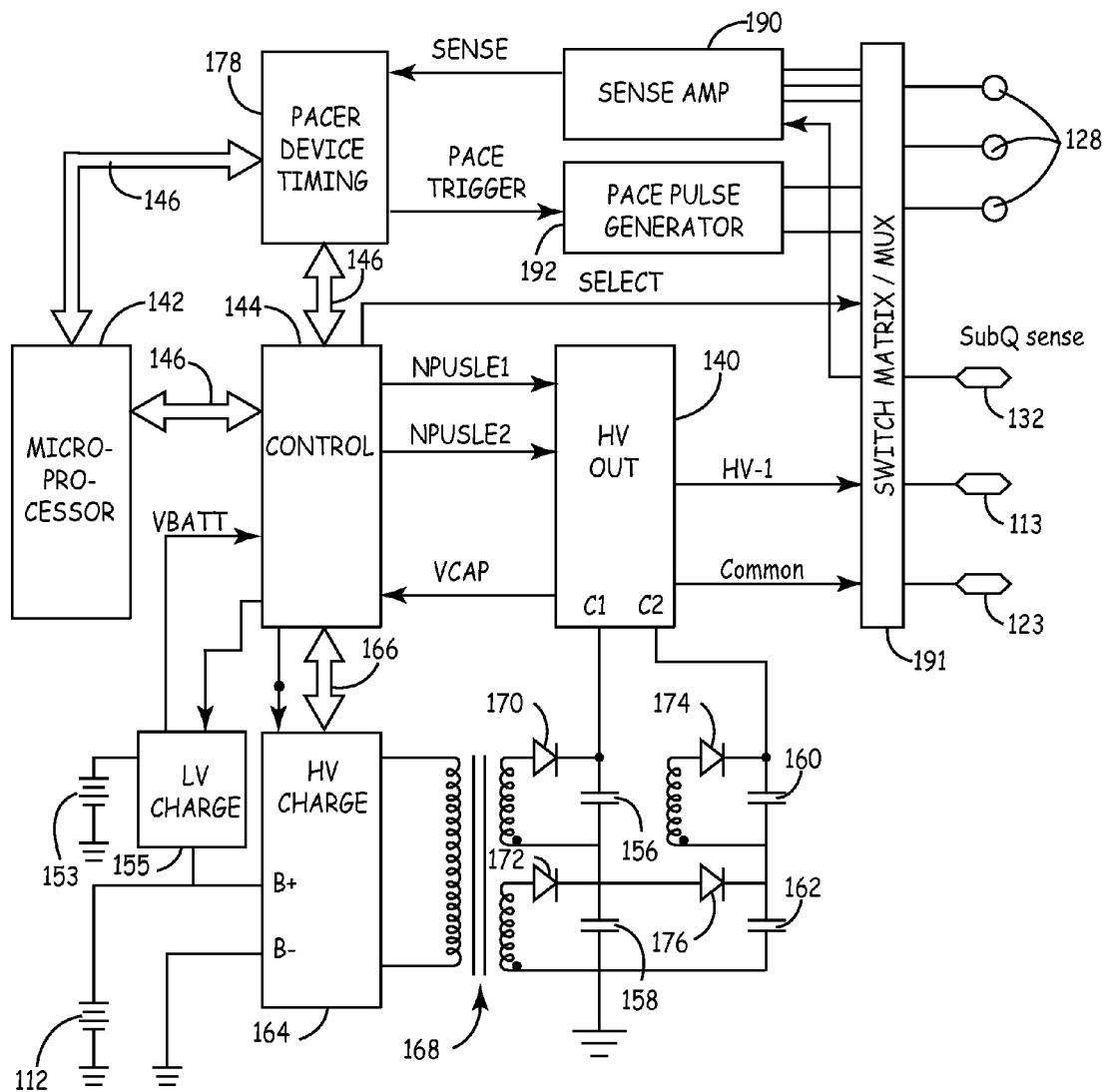
FIG. 3 is a functional block diagram of one embodiment of a SubQ ICD.

FIG. 3 is a functional block diagram of electronic circuitry that may be included in a SubQ ICD, enclosed in the hermetically sealed housing. In FIG. 3 and other functional block diagrams shown and described herein, the described functionality is not limited to any particular type of device architecture and may be implemented using an application specific integrated circuitry (ASIC), electronic circuitry, a processor (shared, dedicated, or group) and memory that execute one or more software or firmware programs, a combinational logic circuit, or other suitable components that provide the described functionality. It is also recognized that all interconnections between functional blocks and other circuitry that may be included in a SubQ ICD, such as a clock and telemetry circuitry, are not specifically shown in FIG. 3.

A battery 112 supplies power to the SubQ ICD 10 circuitry and provides power for generating electrical pulses for pacing or shocking the heart. A second battery 153 may optionally be included for separately providing power for delivering high-voltage shock pulse energy.

SubQ ICD 10 functions are controlled by means of software, firmware and hardware that cooperatively monitor the ECG signals, determine when a cardioversion-defibrillation shock or pacing is necessary, and deliver prescribed cardioversion-defibrillation and pacing therapies. This functionality may correspond to circuitry set forth in commonly assigned U.S. Pat. No. 5,163,427 "Apparatus for Delivering Single and Multiple Cardioversion and Defibrillation Pulses" to Keimel and U.S. Pat. No. 5,188,105 "Apparatus and Method for Treating a Tachyarrhythmia" to Keimel, hereby incorporated herein in their entirety. CV/DF shocks may be delivered employing a housing electrode coupled to the COMMON output 123 of high voltage output circuit 140 and cardioversion-defibrillation electrode 24 (FIG. 1) disposed posterially and subcutaneously and coupled to the output terminal 113 of the high voltage output circuit 140.

In FIG. 3, sense amplifier 190 in conjunction with pacer/device timing circuit 178 processes the subcutaneous ECG sense signal that is developed across a particular ECG sense vector defined by one or more pairs of the subcutaneous electrodes included in SEA 28 (FIG. 2) which are coupled to input terminals 128 and the lead-based sensing electrode 26 (FIG. 2) which is coupled to input terminal 132. The selection of the sensing electrode pair is made through the switch matrix/MUX 191 in a manner to provide the most reliable sensing of the ECG signal(s) Monitoring subcutaneous ECG signals in the presence of noise may be aided by the use of appropriate blanking and extendable refractory periods as described herein below and in U.S. Pat. No. 6,236,882 "Noise Rejection for Monitoring ECGs" (Lee, et al.), hereby incorporated herein by reference in its entirety.

Bradycardia is typically determined by the timing out of an escape interval timer within the pacer timing circuit 178 and/or the control circuit 144. Pace trigger signals are applied to the pacing pulse generator 192 generating pacing stimulation when the interval between successive R-waves (RR interval, also referred to generally herein as "depolarization interval") exceeds the escape interval. Bradycardia pacing may be temporarily provided to maintain cardiac output after delivery of a cardioversion-defibrillation shock that may cause the heart to slowly beat as it recovers back to normal function. Pace pulse generator functions may alternatively be incorporated in the HV output circuitry 140 for delivering pacing pulses of adequate energy for capturing the heart using subcutaneous electrodes.

Detection of a malignant tachyarrhythmia is determined in the microprocessor 142 as a function of the intervals between ventricular depolarizations or R-wave sense signals that are output from the pacer/device timing 178 and sense amplifier circuit 190 to the timing and control circuit 144. Noise contaminated subcutaneous ECG signals are processed by the same sense circuitry via processes and methods as described below. It should be noted that tachyarrhythmia detection may utilize not only interval based signal analysis method but also supplemental sensors and morphology processing methodologies.

Certain steps in the performance of the arrhythmia detection algorithm criteria are cooperatively performed in microprocessor 142, including a microprocessor, RAM and ROM, associated circuitry, and stored detection criteria that may be programmed into RAM via a telemetry interface (not shown). Data and commands are exchanged between microprocessor 142 and timing and control circuit 144, pacer timing circuit 178, and high voltage output circuit 140 via a bi-directional data/control bus 146. Microprocessor 142 is normally asleep but is awakened by interrupt signals to perform any necessary calculations in accordance with a programmed operating mode and implemented algorithms, such as arrhythmia detection algorithms, and to update time intervals monitored and controlled by the timers in pacer/device timing circuitry 178.

Interrupt signals are generated, for example, upon sensing depolarization signals, receipt of downlink telemetry programming instructions, or upon delivery of cardiac pacing pulses to perform any necessary mathematical calculations.

The algorithms and functions of the microprocessor 142 and control circuit 144 employed and performed in detection of tachyarrhythmias may generally correspond, for example, to algorithms disclosed in commonly assigned U.S. Pat. No. 5,354,316 "Method and Apparatus for Detection and Treatment of Tachycardia and Fibrillation" to Keimel; U.S. Pat. No. 5,545,186 "Prioritized Rule Based Method and Apparatus for Diagnosis and Treatment of Arrhythmias" to Olson, et al, U.S. Pat. No. 5,855,593 "Prioritized Rule Based Method and Apparatus for Diagnosis and Treatment of Arrhythmias" to Olson, et al and U.S. Pat. No. 5,193,535 "Method and Apparatus for Discrimination of Ventricular Tachycardia from Ventricular Fibrillation and Treatment Thereof" to Bardy, et al., all of which patents are hereby incorporated herein by reference in their entireties.

The detection algorithms are selected to be particularly sensitive and specific for the presence or absence of life threatening ventricular arrhythmias, e.g., ventricular tachycardia (VT) and ventricular fibrillation (VF). The operational circuitry may be configured to detect the presence of atrial arrhythmias using measured ventricular depolarization intervals as generally disclosed in U.S. Pat. No. 7,031,765 (Ritscher, et al.), hereby incorporated herein by reference in its entirety. Operating modes and parameters of the detection algorithms are programmable. Generally, such detection algorithms are interval based in that the time intervals between successive cardiac depolarizations are measured and compared to arrhythmia detection intervals. A number of interval ranges may be defined corresponding to different tachycardias, for example slow VT, fast VT and VF. In addition to the tachycardia detection intervals, the number of tachycardia detection intervals (NID) that are required to detect a particular tachycardia is also defined. Accordingly, counters for counting the number of successive or non-successive detection intervals out of a previous number of consecutive intervals are used for counting the number of tachycardia detection intervals. If a counter reaches a required NID, the corresponding tachycardia is detected. Separate counters may be provided for slow and fast VT, VF and a combined VT/VF counter may also be provided.

When a malignant tachycardia is detected, high voltage output capacitors 156, 158, 160, and 162 are charged to a pre-programmed voltage level by a high-voltage charging circuit 164 through high voltage transformer 168. Charging is controlled by means of bi-directional control/data bus 166 and a feedback signal VCAP from the HV output circuit 140.

High voltage output capacitors 156, 158, 160, and 162 are discharged through the body and heart between the housing coupled to common terminal 123 and a high voltage coil electrode 24 (shown in FIG. 2) coupled to high voltage terminal 113. Proper charging polarities are maintained by diodes 170, 172, 174 and 176 interconnecting the output windings of high-voltage transformer 168 and the capacitors 156, 158, 160, and 162. As noted above, the state of capacitor charge is monitored by circuitry within the high voltage output circuit 140 that provides a VCAP, feedback signal indicative of the voltage to the timing and control circuit 144. Timing and control circuit 144 terminates a high voltage charge command when the VCAP signal matches the programmed capacitor output voltage, i.e., the CV/DF peak shock voltage.

Control circuit 144 then develops first and second control signals NPULSE 1 and NPULSE 2, respectively, that are applied to the high voltage output circuit 140 for triggering the delivery of cardioverting or defibrillating shocks. Thus, SubQ ICD 10 monitors the patient's cardiac status and initiates the delivery of a CV/DF shock through the cardioversion-defibrillation electrode terminals 113 and 123 in response to detection of a tachyarrhythmia requiring cardioversion-defibrillation. Arrhythmia episode data related to the detection of the tachyarrhythmia and delivery of the cardioversion-defibrillation shock can be stored in RAM included in microprocessor 142 for uplink telemetry transmission to an external programmer to facilitate in diagnosis of the patient's cardiac state.

SubQ ICD 10 includes a telemetry circuit (not shown in FIG. 3), so that it is capable of being programmed by an external device 20 via wireless telemetry link 22 (shown in FIG. 1). Uplink telemetry allows device status and diagnostic/event data to be sent to external programmer 20 for review by the patient's physician. Downlink telemetry allows the external programmer via physician control to allow the programming of device function and the optimization of the detection and therapy for a specific patient. Various telemetry systems for use with an IMD are generally disclosed in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device", all of which are hereby incorporated by reference herein in their respective entireties.

Figure 4:
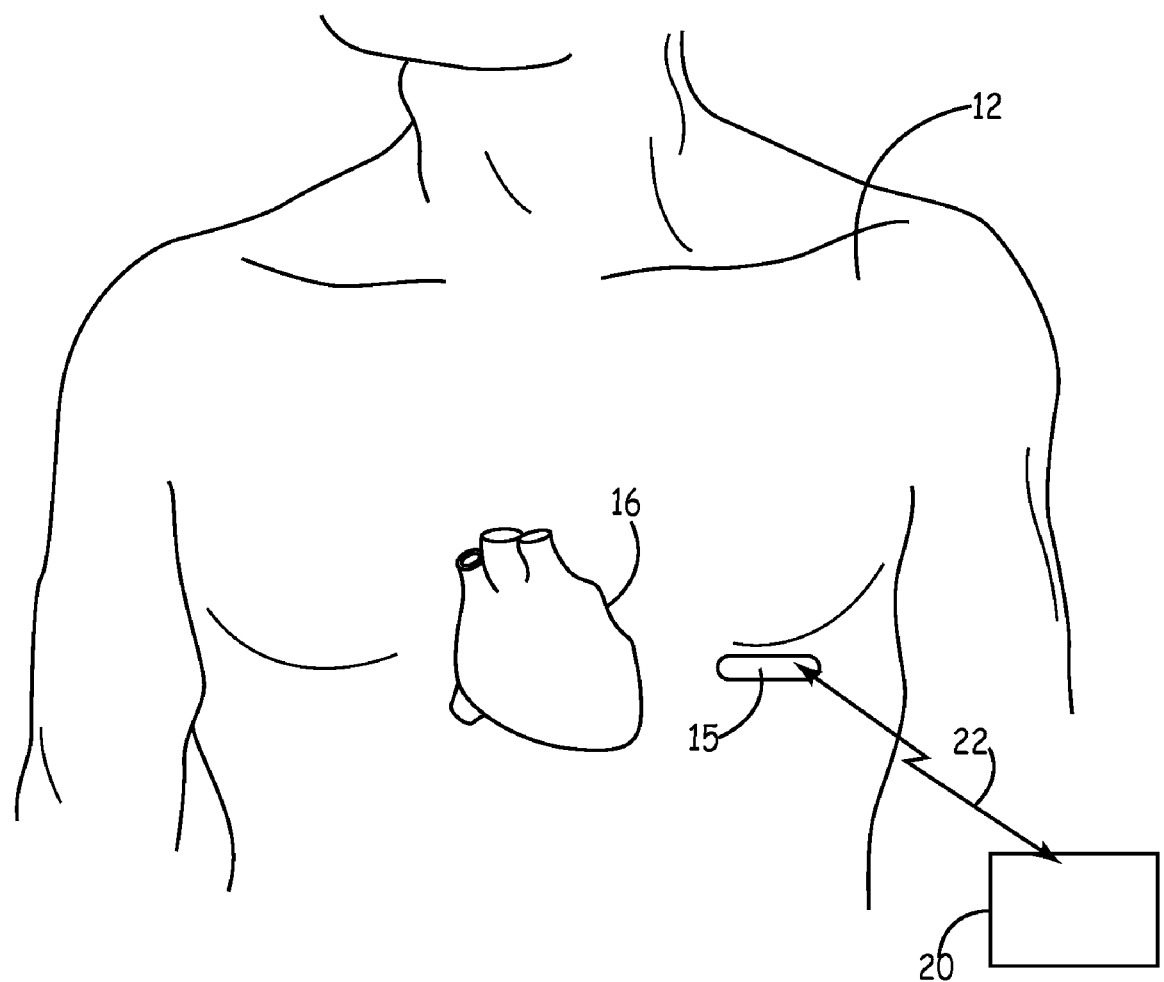
FIG. 4 depicts an ILR implanted in a patient.

FIG. 4 is a frontal view of patient 12 having an ILR 15 subcutaneously implanted. ILR 15 senses cardiac depolarization signals via subcutaneous electrodes (not shown in FIG. 4) from heart 16. A wireless communication link 22 allows bidirectional telemetry communication between ILR 15 and an external device 20, (typically a programmer, home monitor or patient activator) as described previously.

Figure 5:
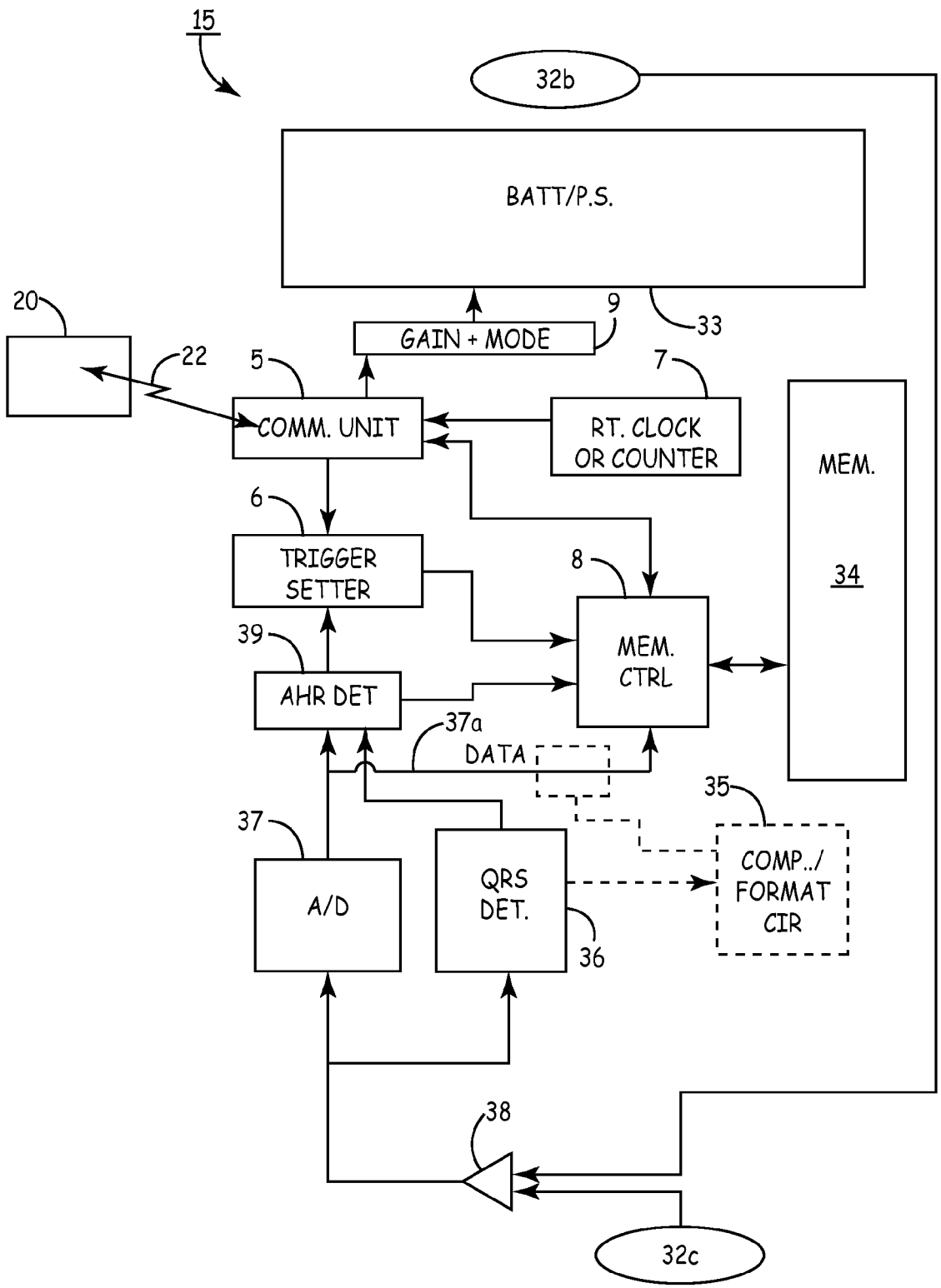
FIG. 5 is a functional block diagram of one embodiment of an ILR.

FIG. 5 illustrates a functional block diagram of ILR 15. ILR 15 includes a battery/power supply 33 for powering the circuitry included in ILR 15. Electrode terminals 32a and 32b bring a signal from the body to an input mechanism 38, here drawn as a differential amplifier for simplicity only, the output of which is fed to a QRS detector 36 and an A/D converter 37. Alternatively, the digitized ECG signal output from A/D converter 37 may be provided as input to QRS detector 36 for detection of depolarization signals using digital signal processing. Both circuits, 36 and 37, may supply an output to an arrhythmia detector 39, which in this embodiment supplies an automatic trigger signal to the trigger setting circuit 6. Subcutaneous ECG signals, including any noise signals, are processed by the amplifier 38, A/D converter 37, QRS detector 36 and arrhythmia detector 39 to provide arrhythmia and noise detection for subsequent evaluation and processing as described herein below. The data output from the A/D converter 37 may be converted, compressed, formatted and marked or reformulated if desired in a circuit 35 before the data is ready for input into the memory 34. The memory control circuit 8 receives input from the A/D converter 37, with or without conversion from circuit 35, from an automatic triggering determination circuit embodied as the arrhythmia detection circuit 39, which may include input directly from the QRS detector 36 if desired, as well as signals from the trigger setter circuit 6.

The trigger setter circuit 6 may also be controlled by a communications unit 5 which operates to receive and decode signals transmitted to ILR 15 via link 22 from external device 20. Register 9 stores gain, mode and rate settings. This communications unit 5 will also be able to communicate with the memory controller 8 to request the offloading of memory data for analysis by external device 20 or another external device. Communications unit 5 includes an antenna and other transceiver device or circuitry to communicate with external device 20. A clock or counter circuit 7 reports the time since start or real time to the external device 20 contemporaneously with a data offloading session so that the events recorded in memory 34 may be temporally pinpointed. ILR 15 may generally correspond to implantable monitoring devices disclosed in U.S. Pat. No. 5,987,352 (Klein, et al.), hereby incorporated herein by reference in its entirety.

Figure 6:
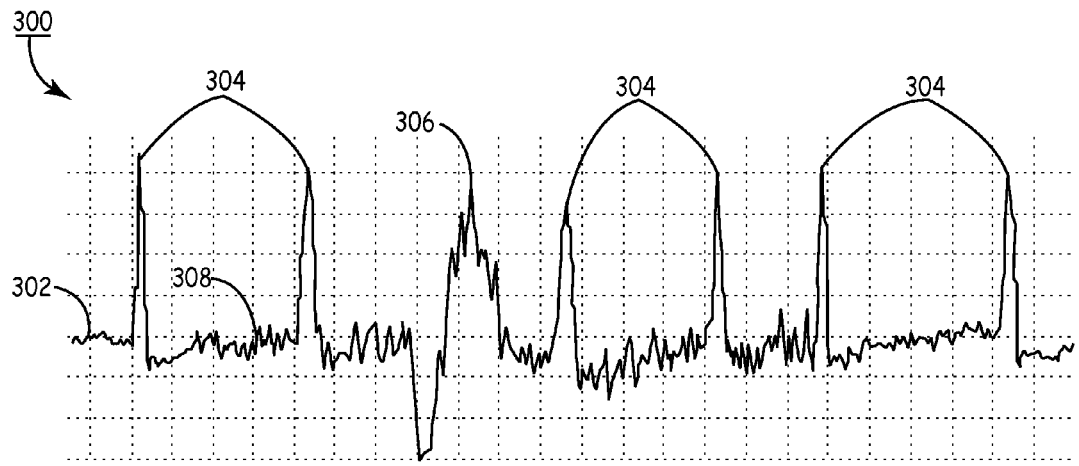
FIG. 6 is an example strip chart recording of an ECG signal incorporating skeletal muscle noise.

FIG. 6 is an example strip chart recording of an ECG signal including noise. Subcutaneously sensed ECG signals are subject to noise due to, for example, non-cardiac myopotentials or electromagnetic interference. Such noise can potentially cause overdetection of tachycardias in IMDs relying on subcutaneous ECG signals. Non-cardiac myopotentials interfering with the ECG signal are caused by skeletal muscle activation in the vicinity of the implanted device. This type of noise can include high-frequency, large amplitude artifacts and can last a several seconds or longer. The recording 300 of FIG. 6 shows an example of non-cardiac myopotential noise 308 present on a subcutaneous ECG 302. High-frequency noise 308 seen on this example exceeds the amplitude of the QRS complexes 304 at 306. Electromagnetic interference (EMI) is typically caused by 50 or 60 Hz conducted or radiated electrical noise from power mains and can be present for relatively long periods of time when a patient is in a "noisy" environment.

Figure 7:
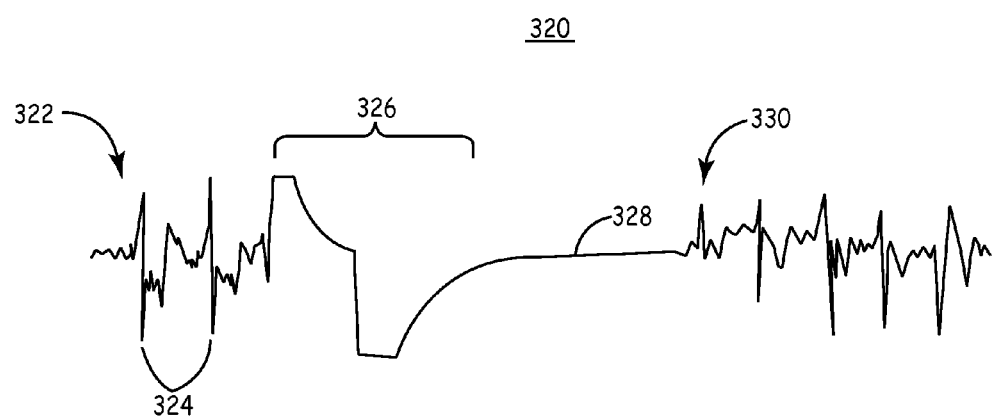
FIG. 7 is an example recording of an ECG signal incorporating an over range signal due to electrostatic discharge or motion artifact.

FIG. 7 is an illustrative recording of an over range noise signal that can occur on a subcutaneous ECG signal. An over range signal can be caused by electrostatic discharge (ESD), electromagnetic interference (EMI), or patient motion artifacts. This situation is characterized by a large common-mode or differential-mode transient that saturates the input amplifier or overflows the input of the A/D converter, preventing the detection of QRS complexes for a period of several seconds, e.g., 5-10 seconds, and thereby causing undersensing of ventricular depolarization signals. Sample recording 320 shows a subcutaneous ECG signal 322 including QRS complexes 324, several seconds of input saturation 326 and an extended period 328 required for the input signal to recover at 330.

While the types of signal interference shown in FIGS. 6 and 7 are more frequently encountered in implantable device systems relying on subcutaneous sensing of physiological signals, the methods described herein are not intended to be limited to subcutaneous applications only. Methods described herein may be implemented in implantable systems which employ electrodes or other physiological sensors disposed at any internal body location. Furthermore, while embodiments described herein relate primarily to cardiac applications involving subcutaneous ECG sensing for arrhythmia detection, methods described herein may be adapted to other physiological signal sensing applications, including intracardiac EGM sensing as well as sensing of other myopotential signals or other physiological signals subject to noise. As such, the devices described above and shown in FIGS. 1-5 above are merely illustrative of the types of devices in which aspects of the present invention may be implemented.

Figure 8:
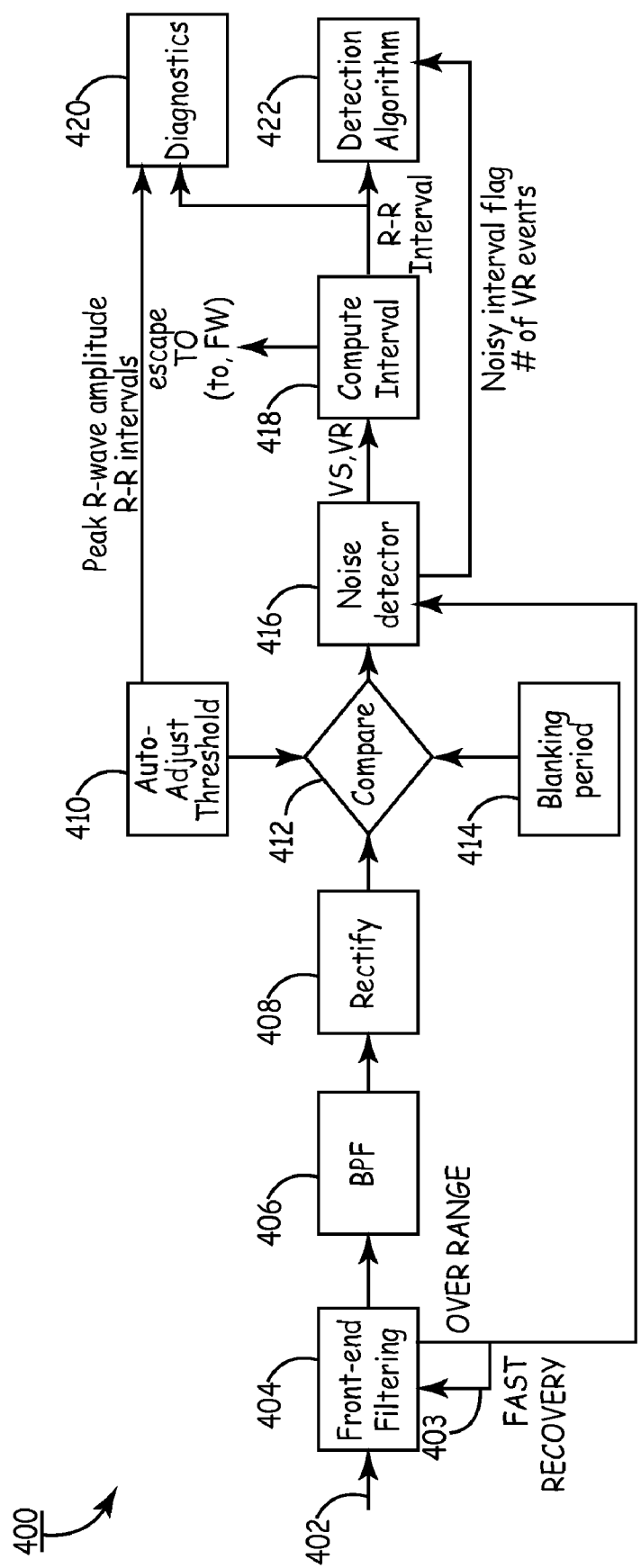
FIG. 8 is a functional block diagram of noise detection methods for use in an IMD according to one embodiment of the invention.

FIG. 8 is a functional block diagram 400 of circuitry included in IMD, such as an ILR or SubQ ICD, for sensing cardiac depolarization signals and measuring depolarization intervals in the presence of noise according to one embodiment of the invention. Methods for detecting noise and responding to noise are described herein primarily with regard to sensing ventricular signals for measuring RR intervals for detecting arrhythmias, which may be ventricular or atrial arrhythmias. However, it is recognized that methods and apparatus described herein may be adapted for use in atrial sensing applications as well wherein PP intervals are measured for detecting arrhythmias. Furthermore, while the methods described herein refer primarily to sensing subcutaneous ECG signals for detecting cardiac depolarization signals, signals acquired using sensing electrodes implanted anywhere in or on the patient's body may be substituted for the subcutaneous ECG signals.

An ECG signal 402 sensed from implanted electrodes is provided as input to filtering block 404 wherein it is amplified, filtered and digitally sampled in front-end filtering block 404. Block 404 is capable of amplifying and processing signals in an expected physiological range of, for example, +/−15 uV to +/−10 mV. The output from front-end filtering block 404 in one embodiment is a 16-bit, 256 Hz sampled signal with a bandwidth of 0.5-95 Hz (as defined by the −3 dB points). The output of filtering block 404 will also be filtered to reject or suppress EMI signals occurring at 50 and 60 Hz via a 50+/−5 Hz and a 60+/−5 Hz notch filter, not shown separately in FIG. 8.

Filtering block 404 monitors for over range signals and generates an over range flag if an over range signal occurs. As used herein, "over range" refers to a signal having an amplitude that saturates an input amplifier or exceeds the amplitude range of the A/D converter. "Over range" also refers to a signal having slew rate exceeding the capability of the A/D converter. Large amplitude noise signals, such as electrostatic discharge and motion artifact, will cause an amplitude over range condition in an input amplifier or the A/D converter. Noise signals having a slew rate higher than the physiological range of cardiac depolarization signals, such as EMI, may not cause an amplitude over range but can exceed the differential limit of the A/D converter. As the A/D converter determines signal sample differentials, a differential exceeding the A/D converter differential limit will cause a rounding off of the difference. If a specified number of signal samples exceed the differential limit out of a given number of signal samples, a differential over range condition occurs and an over range signal is generated by the A/D converter.

An over range flag generated by filtering block 404 is available to noise detector module 416 and detection algorithm module 422 as well as other processing circuitry upon the next interrupt signal. Over range flags are cleared upon every sensed depolarization signal occurring outside a blanking or refractory period. The noise detector module 416 will declare the depolarization interval that ends with the next depolarization signal sensed after the over range flag as a noisy interval. The depolarization interval may be measured as an artificially long interval due to undersensing of depolarization signals during the over range and recovery period.

The diagnostics module 420 may be configured to control storage of marker channel data and will label the next depolarization signal sensed after the over range flag using a marker channel label to indicate a noisy interval (NI) so that a user viewing marker channel data is aware that the preceding depolarization interval is corrupted. A unique marker channel may also be applied to an over range signal. Marker channel data is stored in device memory and can be uplinked to an external device for display. The marker channel is a timeline display of sensed signals (and therapies when delivered), with each signal marker labeled to indicate to a clinician how the sensed signal was classified by the IMD and thus how it was used in arrhythmia detection algorithms, diagnostic metrics, etc. Marker channel operation is generally disclosed in the above-incorporated Markowitz patent.

Upon generating an over range flag, the input amplifier in front-end filtering block 404 is temporarily put into a fast recovery mode 403 to allow the over range signal condition to dissipate rapidly. The fast recovery mode 403 may be applied, for example, for 400 to 850 ms. The fast recovery mode 403 is applied by shorting the differential feedback of the amplifier which causes the amplifier to return to its zero input state as fast as possible. A blanking interval may optionally be applied during the fast recovery mode 403 to prevent spurious sensing.

The digitized data from filtering block 404 is received by a digital bandpass filter 406, for example a Butterworth filter having cut-off frequencies at 10 Hz and 32 Hz. In one embodiment, the 10 Hz high-pass cutoff has two poles of rolloff, and the 32 Hz low-pass cutoff has 6 poles of rolloff. The output of bandpass filter 406 is provided to rectifier 408 where the signal is rectified such that the signal is always greater than zero in order to simplify the comparison to an automatically adjusted sensing threshold generated by module 410.

The filtered, rectified ECG signal is compared to the automatically adjusted sensing threshold by comparator 412. The auto-adjusted sensing threshold module 410 and comparator 412 provide depolarization signal detection as generally described in U.S. Pat. No. 5,117,824 "Apparatus for Monitoring Electrical Physiologic Signals" (Keimel, et al.); U.S. Pat. No. 7,027,858 "Method and Apparatus for Cardiac R-wave Sensing in a Subcutaneous ECG Waveform" (Cao, et al.) and U.S. Publication No. 2004/0260350 "Automatic EGM Amplitude Measurements During Tachyarrhythmia Episodes" (Brandstetter, et al.), all of which are incorporated herein by reference in their entireties. Generally, following a sensed depolarization signal, the sensing threshold is automatically adjusted so that the effective sensing threshold is set equal to a proportion of the amplitude of the sensed depolarization signal. The effective sensing threshold decays thereafter to a lower or base-sensing threshold. For example, an R-wave sensing threshold generated by auto-adjusting sensing threshold module 410 is automatically adjusted to a percentage of the amplitude of sensed R-waves. This ensures that R-wave sensing operates correctly over a range of R-wave amplitudes. Additionally, since T- and P-wave amplitudes are typically correlated with the R-wave amplitude, a threshold that is automatically adjusted based on a sensed R-wave amplitude will typically provide some protection against T- and P-wave oversensing.

Figure 9:
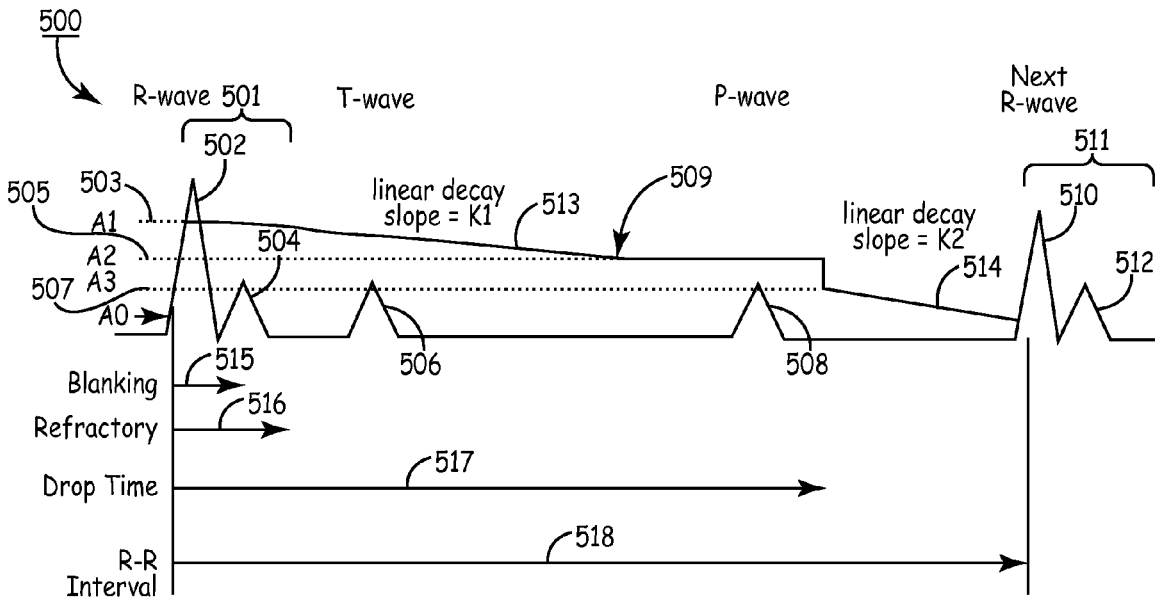
FIG. 9 is a timing diagram showing ECG depolarization signal detection in accordance with one embodiment of the present invention.

FIG. 9 is a diagram illustrating one embodiment of a method for automatically adjusting a sensing threshold for discriminating R-waves from other electrical signals. Specifically, a multi-level sensing threshold is used employing different linear decay rates to lower the sensing threshold from one level to the next.

Diagram 500 illustrates a filtered, rectified R-wave 501 having first and second signal portions 502 and 504, a T-wave 506, a P-wave 508 and a next filtered, rectified R-wave 511 having first and second portions 510 and 512. R-wave 501 is sensed when first portion 502 exceeds a previously adjusted sensing threshold amplitude A0. In response to sensing R-wave 501, sensing threshold 509 is automatically adjusted to a first amplitude (A1) 503 based on a percentage of sensed R-wave 501. The percentage is typically programmable, for example between 40 and 75% and may be nominally set at 65% of the sensed R-wave amplitude. Upon sensing R-wave 501, a blanking interval 515, refractory period 516, drop time 517 and a depolarization interval (RR interval) timer 518 are started. Sensing threshold 509 stays constant for at least blanking interval 515, an optionally longer according to predetermined threshold hold time (not shown in FIG. 9). The blanking interval 515 and a threshold hold time when implemented reduce the likelihood of sensing the second portion 504 of R-wave 501, which otherwise results in "double-sensing" R-wave 501, and T-wave sensing. Sensing threshold 509 then begins a linear decay 513 to a next sensing threshold amplitude (A2) 505. Upon reaching threshold amplitude A2 505, the auto-adjusting threshold stops decreasing and stays constant at the amplitude A2 505 until the drop time 517 has timed out. Upon expiration of drop time 517, sensing threshold 509 drops abruptly to a third amplitude (A3) 507 and begins another linear decay 514, which may be a more rapid decay rate than the rate of the previous linear decay 513, to allow sensing of the subsequent R-wave 511. A depolarization interval is then measured as the time accumulated in RR interval timer 518 from sensed R-wave 501 until the next sensed R-wave 511.

The multi-level auto-adjusting threshold 509 minimizes double sensing of wide R-waves and minimizes oversensing of T-waves and P-waves while enhancing the sensing of R-wave signals, particularly low amplitude R-wave signals encountered in subcutaneous ECG signals. A maximum limit is imposed on the initial auto-adjusted amplitude A1 503 to prevent a high amplitude noise signal from setting the initial threshold A1 503 to an unrealistically large value.

Referring again to FIG. 8, comparator 412 compares the filtered/rectified ECG signal amplitude, the auto-adjusted sensing threshold provided by module 410, and a blanking interval generated by block 414 (and shown in FIG. 9). When a signal sample exceeds the sensing threshold outside of a blanking interval, noise detector module 416 determines if the signal is within a refractory period. If not, a ventricular sense (VS) interrupt signal is generated by noise detector module 416 and provided to the compute interval block 418 for use in measuring an RR interval.

The VS interrupt restarts the auto-adjusting threshold operation with the sensing threshold being reset to a percentage of the sensed R-wave peak amplitude. The R-wave peak amplitude may be defined as the largest amplitude seen in the filtered/rectified signal during the blanking interval. ECG signal samples during the blanking interval that exceed the sensing threshold do not cause a VS interrupt signal, do not generate a marker to be displayed on a marker channel, and do not cause the auto-adjusted sensing threshold to be reset. The blanking interval is nominally active for a predetermined interval, e.g., 70 ms following a sensed depolarization (VS), but is programmable from, for example, 50-120 ms by the implanting physician. Note that this blanking interval is "output blanking" only, meaning it is not applied to the input amplifier or any of the signal processing blocks preceding the comparator 412.

Noise detector module 416 monitors for signals sensed during a refractory period for detecting noisy depolarization intervals. When the output of comparator 412 indicates a sensed signal has occurred outside the blanking interval and noise detector 416 determines the sensed signal is within a refractory period, a refractory sense (VR) interrupt signal is generated and provided to compute interval block 418. In response to a VR interrupt, compute interval block 418 ignores the sensed signal for computing an RR interval.

Figure 10:
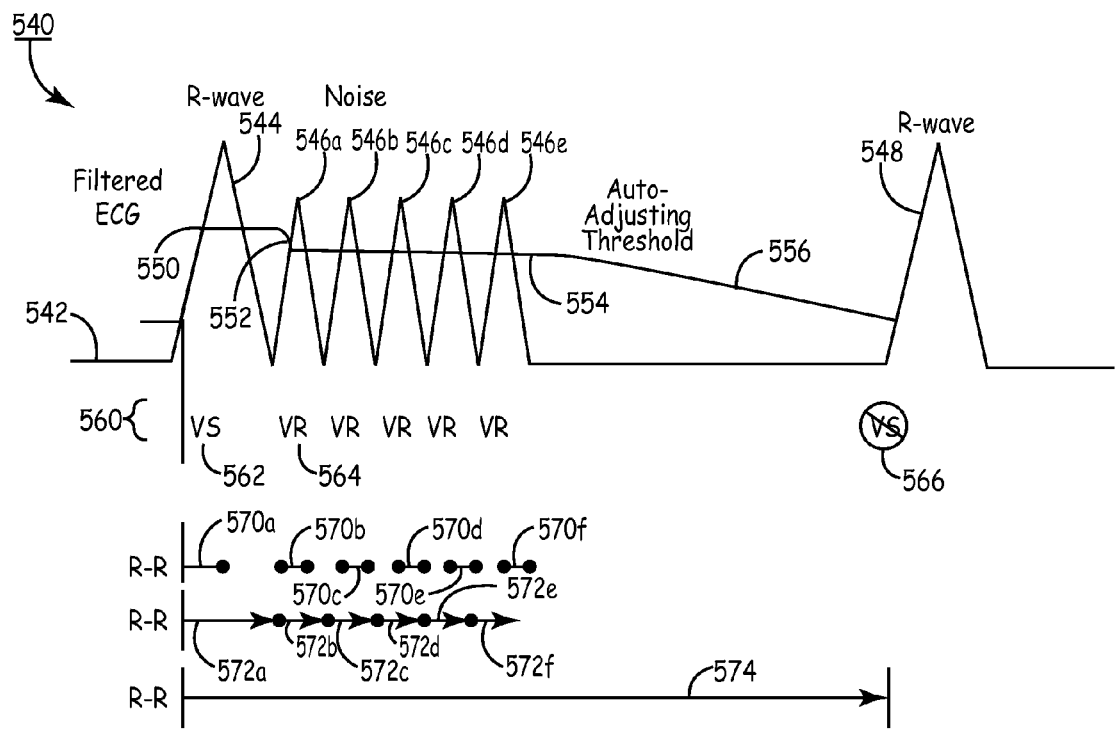
FIG. 10 is a timing diagram showing noise detection in accordance with one embodiment of the present invention.

FIG. 10 is a diagram illustrating one method for detecting a noisy depolarization interval according to one embodiment of the invention. An R-wave 544 is sensed when a filtered, digitized and rectified ECG signal 542 exceeds an auto-adjusted sensing threshold amplitude outside of a blanking interval or refractory period. This non-refractory sensed signal (R-wave 544) generates a VS interrupt and is denoted as a VS event 562 on a marker channel output 560.

The sensed R-wave 544 initiates a blanking interval 570a, a refractory period 572a, and starts a timer for measuring RR interval 574. The refractory period 572a is programmable, e.g., between 120 and 180 ms and may be nominally set, e.g., at 130 ms in one embodiment. If the next sensed signal falls within the refractory period 572a, it is assumed to be due to noise since an RR interval less than the selected refractory period 572a is considered to be too fast to be physiologic.

Accordingly, a signal 546a crossing the auto-adjusted sensing threshold 550, after blanking interval 570a but before refractory period 572a has expired, will generate a VR interrupt and be labeled as a VR event 564 on marker channel 560. A timer measuring RR interval 574 is not reset by the VR event 546a. A blanking interval 570b will be restarted in response to the VR interrupt signal, and the auto-adjusted sensing threshold 550, which began a linear decay 552 after the initial blanking interval 570a, will be reset to an amplitude 554 based on the peak amplitude of the refractory sensed signal 546a.

A refractory period 572b is also restarted in response to the refractory sensed signal 546a. The refractory period 572b started in response to the refractory sensed signal 546 may be shorter, e.g. 100 ms, than the initial refractory period 572a set in response to the non-refractory sensed signal 544. A series of refractory sense signals 546a through 546e are sensed during refractory periods 572a through 572e, respectively, resulting in reset blanking periods 570b through 570f and reset refractory periods 572b through 572f as illustrated in FIG. 10. In this way, sustained noise signals present for an unknown duration of time, for example non-cardiac myopotentials, can be sensed as repetitive VR events 546a through 546e, effectively inhibiting R-wave sensing and erroneous RR interval measurement until the sustained noise signals are no longer present.

After the final blanking interval 570f expires, the auto-adjusted sensing threshold 550 will begin a linear decay 556. A next non-refractory sense signal 548 is sensed upon crossing the auto-adjusted sensing threshold 550.

In accordance with one embodiment of the invention, whenever two or more refractory sense signals 546a through 546e occur between two non-refractory sense signals 544 and 548, the RR interval 574 defined by the non-refractory sense signals 546 and 548 will be declared a noisy interval by noise detector module 416. The minimum number of refractory sense signals required to declare a noisy interval is nominally 2 in one embodiment and may be programmable, e.g., from 1 to 4. A noisy interval is denoted to a user on marker channel output by applying a unique marker channel label 566 to the non-refractory sense signal 548 defining the end of the noisy depolarization interval 574. In the embodiment shown, the unique marker channel label for a noisy interval is depicted as an encircled "VS" with a slash or strikethrough through it, indicating the non-refractory sensed signal terminates a noisy interval that will not be used in the same way as a non-noisy interval for detecting arrhythmia events and computing diagnostics.

Referring again to FIG. 8, a noisy interval flag generated in response to VR events by noise detector module 416 is provided to compute interval block 418 which computes the length of the noisy interval and provides the noisy interval length to diagnostics module 420. Noise detector module 416 also monitors for an over range flag (generated by filtering block 404) present upon sensing a non-refractory depolarization signal. If an over range flag is present upon sensing a non-refractory signal, the RR interval ending upon the non-refractory sense signal is declared to be a noisy interval. Noise detector module 416 generates a noisy interval flag provided to the compute interval block 418 such that the noisy interval may be measured and used for noise diagnostic purposes. A unique marker channel label is applied to the non-refractory sense signal ending the RR interval during which the over range flag was present.

The compute interval block 418 computes intervals between two non-refractory sensed events for use in detecting arrhythmias when the interval has not been declared a noisy interval. The detection algorithm module 422 receives non-noisy depolarization intervals for use in detecting algorithms and receives noisy interval flags such that noisy intervals can be used by detection algorithm module 422 to inhibit arrhythmia event detection based on noisy intervals. Escape time-out events may be generated by the compute interval block 418 at a selected time interval following a non-refractory sensed signal, for example at about 2 seconds, when no non-refractory sensed signal occurs.

The noise detector 416 and compute interval block 418 generate interrupt signals corresponding to non-refractory sensed signals (VS), refractory sense signals (VR), escape time out (TO) events (which are generally not indicated by a marker on the marker channel), and noisy interval flags. Firmware (FW) or other implemented functional circuitry, including detection algorithm module 422 and diagnostics module 420, uses data available upon the interrupt signals to make calculations and execute algorithms for arrhythmia event detection, diagnostic, and therapy delivery (if present) functions.

Upon each VS interrupt signal, the current RR interval length, number of VR events during the RR interval, peak R-wave amplitude from the leading R-wave of the RR interval, and any over range flags are made available to firmware or other functional circuitry. Upon each VR interrupt signal, the number of VR events in the current RR interval is made available. If the number of VR events meets or exceeds the noisy interval criteria or an over range flag is set, the next non-refractory sensed signal is labeled as a noisy interval as described above.

The RR interval measured at block 418 is used by detection algorithm module 422 for detecting arrhythmia events. The inputs to the detection algorithm module 422 include VS signals, RR intervals, noisy interval flags, and the total number of refractory sense events in the most recent RR interval. Detection algorithm module 422 inhibits detection of an arrhythmia event in response to a noisy interval. The onset and the termination of any arrhythmia that the IMD is configured to detect are referred to herein collectively as an "arrhythmia event". The detection algorithm inhibits the detection of an arrhythmia onset or termination by decreasing event counters in response to a noisy interval flag.

Decrementally adjusting event counters in response to a noisy interval prevents detecting the start or end of an arrhythmia episode based on noisy data, while still allowing for detection to occur in the presence of noise. Additionally, it "slows down" the detection algorithm enough that short-duration noise (such as myopotentials) can end before a detection is made without completely interrupting the detection process. An event counter may be decreased by one or more in response to a noisy interval, and different counters may be configured to be decremented by a different amount in response to a noisy interval. It is further contemplated that an event counter may be held at its present value, i.e. neither incremented nor decremented, in response to a noisy interval.

The detection algorithm module 422 detects asystole by accumulating the time interval between a non-refractory sensed signal and a subsequent escape time-out event and/or a subsequent non-refractory sensed signal. If the accumulated time exceeds an asystole detection threshold, asystole is detected and the asystole episode data is provided to diagnostics module 420.

If an over range flag occurs during an accumulated asystole time interval, the asystole episode may still be detected if the accumulated time interval has already exceeded the asystole detection threshold at the time the over range signal occurred. If a noisy interval is detected based on two or more refractory sensed signals, asystole is not detected. The asystole timer is restarted upon the next escape time out event or the next non-refractory sensed signal following the last refractory sensed signal.

Asystole termination is detected upon measuring a predetermined number of RR intervals or sensing a predetermined number of non-refractory signals. For example, asystole termination may be detected upon measuring four RR intervals. If an asystole episode is in progress, a noisy interval will inhibit detection of asystole termination. In one embodiment, a noisy interval will cause an RR interval counter used for detecting asystole termination and having a counter value of greater than zero to be decreased by one.

The diagnostics module 420 utilizes the peak R-wave from the most recent non-refractory sensed signals to generate R-wave amplitude histograms. Additionally, marker channel markers (i.e., VS, VR, noisy interval), escape timeouts (TO), detected asystole events, current RR interval information, the number of refractory sensed signals in the current RR interval, and any flags indicating an over range condition will be input to diagnostics module 420 for storage and later retrieval for display on an external device.

As will be described below, diagnostics module 420 will utilize this data for generating noise diagnostics in addition to other diagnostic data relating to detected R-waves, RR intervals, and arrhythmia event detections. Briefly, diagnostics module 420 may determine a noise burden metric, e.g., the total number or duration of depolarization intervals declared as noisy intervals, a snapshot of the ECG signal including declared noisy intervals, and the time and date of noisy intervals. Additionally, trends of the number of noisy intervals and/or histograms of sensed depolarization signal amplitudes and noise signal amplitudes may be generated.

Figure 11:
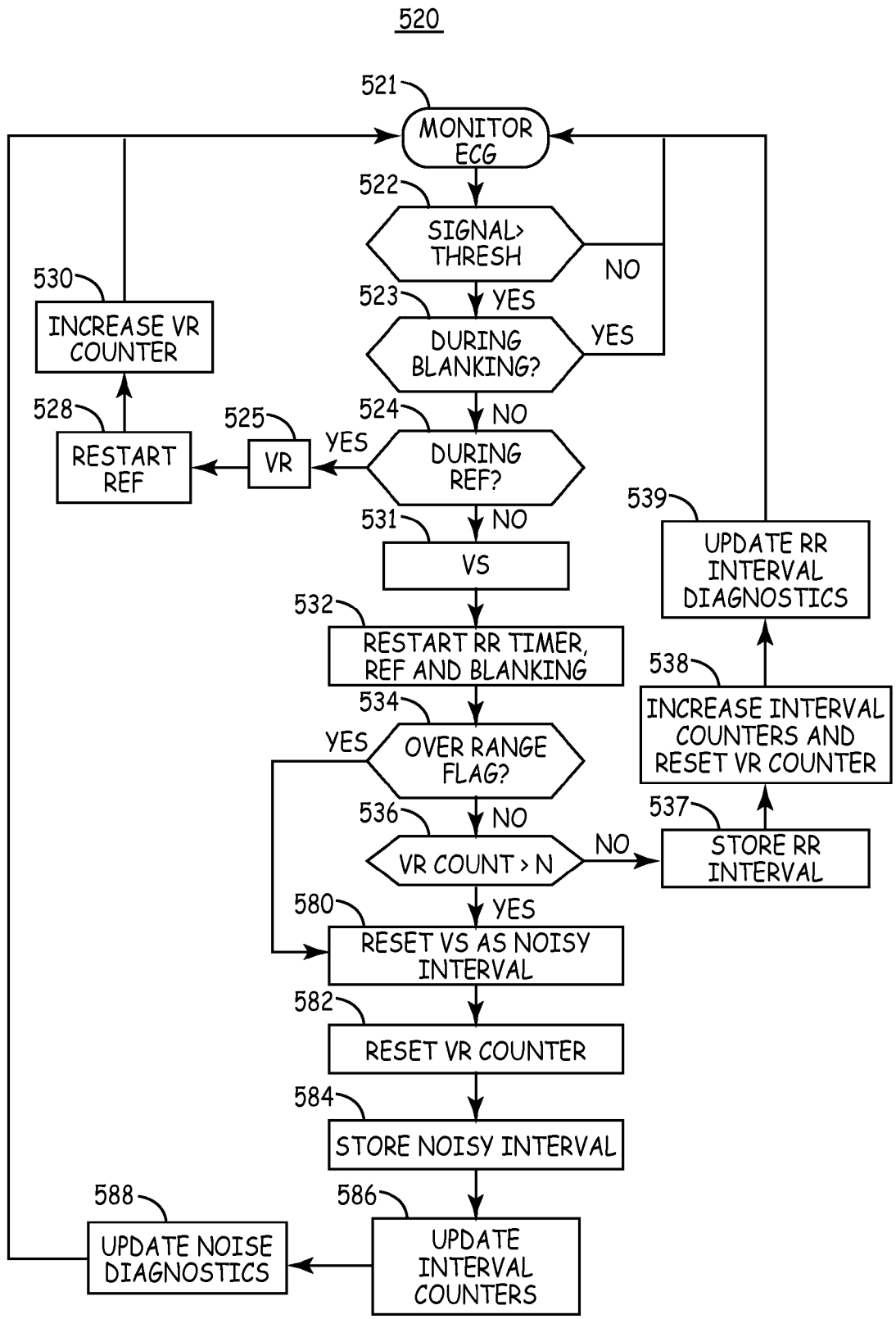
FIG. 11 is a flow chart of one method for detecting and responding to noisy intervals during EGM/ECG sensing in accordance with the present invention.

FIG. 11 is a flow chart 520 illustrating one method for detecting noisy intervals during EGM/ECG sensing and differentiation of cardiac and noise signals by the IMD in accordance with the present invention. Flow chart 520 is intended to illustrate the functional operation of the device, and should not be construed as reflective of a specific form of software or hardware necessary to practice the invention. It is believed that the particular form of software will be determined primarily by the particular system architecture employed in the device and by the particular detection and therapy delivery methodologies employed by the device. Providing software to accomplish the present invention in the context of any modern implantable medical device, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

ECG signals are monitored using selected electrodes at block 521, and filtered, digitized and rectified. At block 522, the filtered, digitized and rectified ECG signal is compared to a sensing threshold, which is generally an auto-adjusted threshold as described previously. When a signal sample exceeds the sensing threshold at block 522, the IMD determines if the sample occurred during a blanking interval at block 523. If a blanking interval is active, the signal is ignored, and method 520 returns to block 521 to continue monitoring the ECG signal.

If the threshold crossing at block 522 occurs outside a blanking interval but during a refractory period as determined at block 524, a VR interrupt signal is generated and the refractory sensed signal is labeled as a VR event at block 525. A refractory period is restarted at block 528. A VR counter is increased by one at block 530 for use in detecting a noisy interval. The VR counter is increased for each VR sensed since a preceding VS. The IMD continues monitoring the ECG by returning to block 521.

If a signal sample crosses the sensing threshold a refractory period, a VS interrupt signal is generated and the non-refractory sensed signal is labeled as a VS event at block 531. An RR interval timer, refractory period and blanking interval and any other timing intervals such as the drop time used for auto-adjusted sensing threshold generation are restarted at block 532. Before adjusting interval counters used for detecting arrhythmias in response to the VS event, the RR interval ending with the VS event is examined to distinguish between noisy and valid RR intervals.

At block 534, the IMD determines if an over range flag is present upon the VS interrupt signal. If an over range signal has been detected prior to the VS event and after the most recent previous VS event, the current RR interval is declared a noisy interval and the VS marker is reset as a noisy interval marker at block 580. If no over range flag is present but the VR counter exceeds a noise detection threshold, N, as determined at block 536, a noisy interval is declared at block 580. The VS label is reset as a noisy interval label at block 580, and the VR counter is reset to zero at block 582 to start counting again from zero for the next RR interval.

If the interval is not determined to be noisy, the length of the RR interval defined by the current and preceding VS events is stored at block 537. Various interval counters are updated at block 538 in response to the valid RR interval. The counters that are increased will depend on the RR interval length and may include onset and termination detection counters corresponding to bradycardia, asystole (termination counter only), slow VT, fast VT, VF, a combined VT/VF counter, as well as interval counters used in detecting atrial arrhythmias based on ventricular depolarization intervals. The VR counter is reset to zero at block 538 to start counting again from zero following the VS event.

The RR interval stored at block 537 is also used to update diagnostic metrics relating non-refractory sensed signals at block 539. Such diagnostic metrics may include, for example, R-wave amplitude trends and RR interval or heart rate histograms. In this way, valid R-waves and RR intervals determined to be free of noise are used in determining diagnostic metrics, and RR intervals declared to be noisy intervals in response to over range or refractory sensed signals are excluded from the computation of diagnostic metrics relating to R-waves and RR intervals. As described below, RR intervals declared to be noisy will be used for determining noise diagnostic metrics instead. The IMD continues monitoring the ECG at block 521 and responds to the updated interval counts at block 538 by triggering ECG signal storage and/or therapy delivery as appropriate whenever arrhythmia event detection criteria are met.

If the RR interval is declared a noisy interval (block 580), the length of the noisy interval is stored at block 584. At block 586, arrhythmia event detection, including both onset and termination events, is inhibited by holding or decrementing any interval counters that are greater than zero. Any onset or termination counters corresponding to bradycardia, asystole (termination counter only), slow VT, fast VT, VF, combined VT/VF, and atrial arrhythmia detection are decreased by an assigned decrement, which may be zero, one, or more. This adjustment effectively slows the arrhythmia event detection process to allow transient noise to pass before detecting an arrhythmia event without interrupting a detection process and avoiding a detection made based on noisy data.

In some cases, arrhythmia detection criteria may be based on detecting a number of consecutive intervals meeting a defined detection interval range. In such cases, the interval counter may be merely decreased by an assigned decrement in response to a noisy interval. In other cases, for example for detecting VF, the detection criteria may be based on detecting a defined number of detection intervals out of a defined number of preceding intervals. As such, the VF detection intervals may not be consecutive but do fall within a given number of preceding RR intervals. In this case, in order to decrease the VF counter by one, the most recent VF detection interval, which may not be the most recent RR interval but is an interval falling into a defined VF detection zone, is reclassified as a non-detection interval, i.e., an interval that is not counted for meeting number of intervals required to detect VF. One or more VF detection intervals may be reclassified as non-detection intervals upon each noisy interval declaration.

A combined VT/VF counter may also be used for arrhythmia detection and may be implemented as the sum of the individual VT and VF counters. If both the VT and VF counters are greater than zero at the time of a noisy interval declaration, only one of the VT and VF counters, e.g. the VT counter, is decremented in response to the noisy interval to avoid decrementing the combined VT/VF counter twice for the same noisy interval.

The stored noisy interval is also used for determining noise diagnostics at block 588. The determination of noise diagnostics will be described in detail in conjunction with FIG. 13. The IMD continues monitoring the ECG by returning to block 521.

Figure 12:
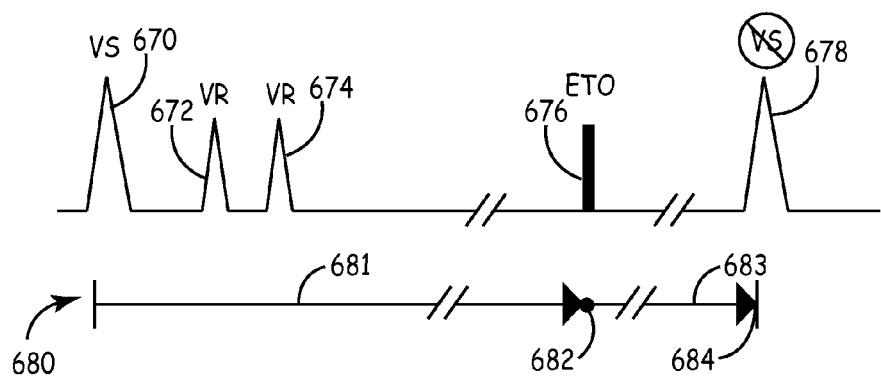
FIG. 12 is a diagram illustrating the function of an asystole timer in the presence of noisy intervals according to one embodiment of the invention.

FIG. 12 is a diagram illustrating the function of an asystole timer in the presence of noisy intervals according to one embodiment of the invention. A non-refractory sensed signal 670 is followed by two or more refractory sensed signal 672 and 674 causing the next non-refractory sensed signal 678 to be labeled as a noisy interval. An asystole detection timer 680 is initiated upon sensing the first VS event 670. Upon the next interrupt signal following the last VR event 674, the asystole detection timer 680 is restarted. The next interrupt signal may be generated upon an escape time out event 676 or the next VS event 678, whichever comes first. Upon the next interrupt signal, the number of VR events 672 and 674 since the last VS event 670 are compared to the required number for declaring a noisy interval. If the number of VR events exceeds the number required for declaring a noisy interval, the asystole detection timer 680 is restarted in response to the interrupt signal. An asystole onset detection is not made regardless of the value of the asystole timer 680 at the time of the interrupt signal due to the presence of noise.

For example, the asystole detection timer 680 is restarted at 682 in response to the escape time out event 676. The interval 681 between the VS event 670 and the escape time out 676 is cleared from an accumulated asystole time. Upon the next interrupt signal at non-refractory sensed event 678, the interval 683 between the escape time out 676 is compared to an asystole detection threshold. If the interval 683 exceeds the asystole detection threshold, an asystole detection is made at 684. Even though the interval between VS 670 and the next non-refractory sense 678 is declared a noisy interval due to the VR events 672 and 674, a portion 683 of the entire noisy interval may still be used to detect asystole.

If the asystole detection threshold has not yet been met upon the non-refractory sense event 678, the asystole detection timer 680 is restarted at 684 and no asystole detection is made. If an escape time out interrupt 676 does not occur after the last refractory sense 674 and before the next non-refractory sensed signal 678, the asystole detection timer 680 is restarted at 684 and the entire noisy interval between the two non-refractory sense signals 670 and 678 is not used for detecting an asystole event even if the noisy interval exceeds the asystole detection threshold.

Figure 13:
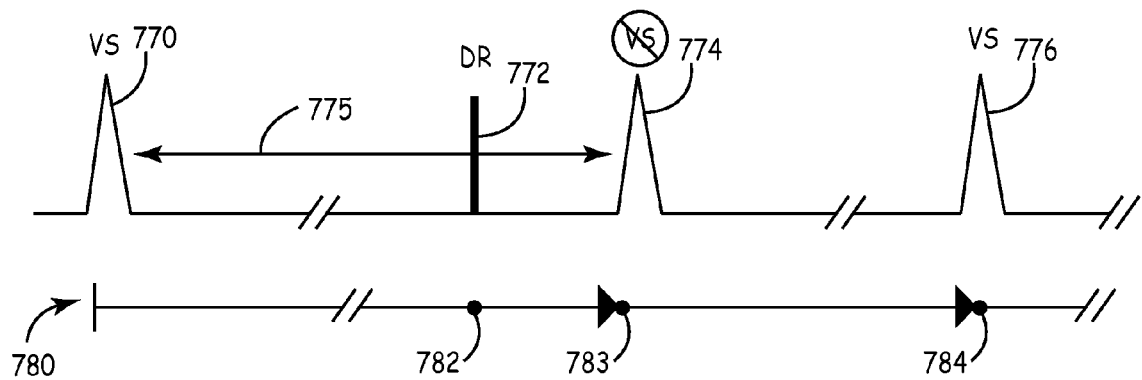
FIG. 13 is diagram illustrating the function of an asystole timer in the presence of over range signals according to one embodiment of the invention.

FIG. 13 is diagram illustrating the function of an asystole detection timer in the presence of over range signals according to one embodiment of the invention. A non-refractory sensed signal 770 starts an asystole detection timer 780. Upon generation of an over range flag 772, the asystole detection timer is compared to an asystole detection threshold. If the asystole detection timer meets or exceeds the asystole detection threshold at the time of the over range flag 772, an asystole detection is made at 782. A separate asystole duration timer may continue to accumulate time until the next non-refractory sense 776 that is not labeled as a noisy interval. The first non-refractory sensed signal 774 following the over range flag 772 is labeled as a noisy interval and restarts the asystole detection timer 780. However, the first non-refractory sensed signal 774 may not cause an asystole duration timer (not shown) to be restarted. A separate asystole duration timer may continue to accumulate time until the first non-refractory sense event 776 after the noisy interval 775 or until an asystole termination criteria is met. Delaying resetting an asystole duration timer inhibits detecting termination of asystole due to undersensing during an over range signal and recovery period.

If the asystole detection timer 780 does not meet or exceed an asystole detection threshold at the time of the over range flag 772, asystole is not detected. The asystole detection timer 780 is restarted at 783 upon the first non-refractory sense signal 774 following the over range flag 772.

Figure 14:
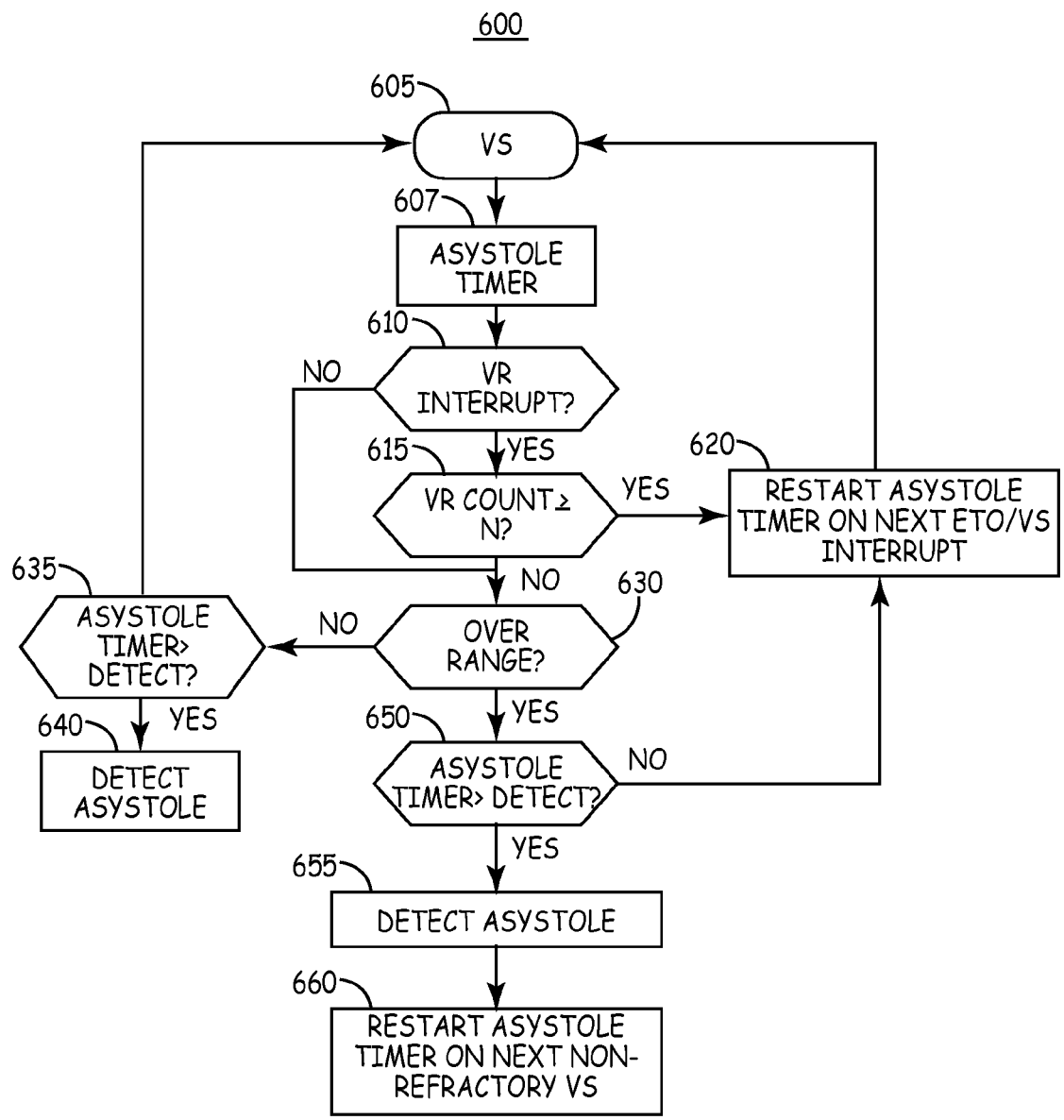
FIG. 14 is a flow chart of a method for detecting asystole in the presence of noise.

FIG. 14 is a flow chart of a method 600 for detecting asystole in the presence of noise. The detection of a non-refractory VS event at block 605 starts an asystole detection timer at block 607. A separate asystole duration timer may optionally be started at block 607. If a VR interrupt is generated in response to a refractory sensed signal, at block 610, a VR counter is compared to a noisy interval threshold, N, at block 615. If the VR count meets or exceeds the noisy interval threshold, the asystole timer is restarted on the next escape time out event or VS interrupt at block 620. Asystole is not detected regardless of the value of the asystole timer at the timer of the VR interrupt.

If an over range flag is generated at block 630 in response to an over range condition, the asystole detection timer is compared to an asystole detection interval at block 650. If the accumulated time in the asystole detection timer has already met the asystole detection criteria at the time of the over range flag, asystole is detected at block 655. A separate asystole duration timer may continue accumulating time in the asystole timer until the next VS interrupt that is not associated with a noisy interval. As such, the over range flag allows asystole detection to still be made if detection criteria have already been met. The first VS event associated with the interval declared noisy in response to the over range flag, however, may not be used to reset an asystole duration timer or counted by an asystole termination counter.

If the asystole detection threshold has not yet been reached at the time of the over range flag, as determined at block 650, the asystole detection timer is restarted on the next escape time out or VS event at block 620 without detecting asystole. If no over range flag is generated, method 600 accumulates time in the asystole detection timer until the asystole detection threshold is met (block 635) and asystole is detected (block 640), or the next VS event occurs at block 605.

Figure 15:
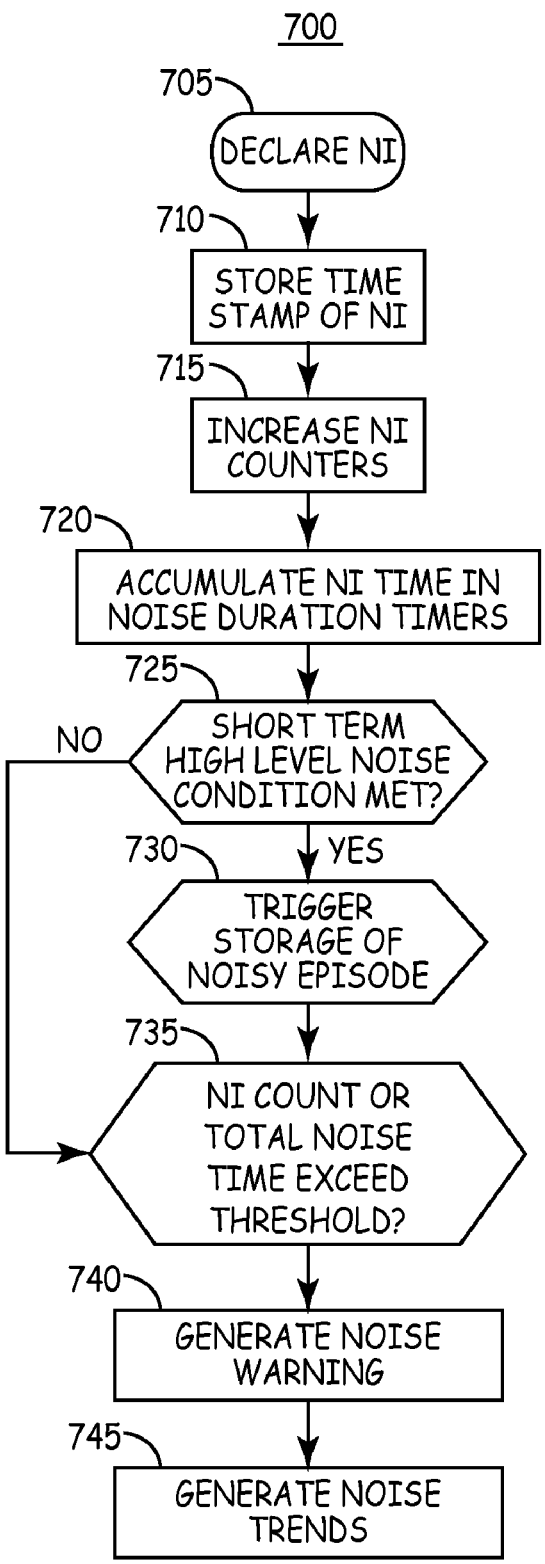
FIG. 15 is a flow chart of a method for determining and presenting noise diagnostics.

FIG. 15 is a flow chart of a method 700 for determining and presenting noise diagnostics. At block 705, a noisy interval (NI) is declared based on the detection of a required number of VR events or an over range flag as described previously. At block 710, the time and date stamp of the noisy interval is stored such that the time of noisy intervals are accessible and can be reviewed by a clinician upon interrogating the IMD.

At block 715, one or more noisy interval counters having varying time resolution are increased in response to the noisy interval declaration. For example, noisy interval counters corresponding to a 30 second time interval, one day, and the total time since device implant or the most recent device interrogation session may be included. Each noisy interval counter counts the number of RR intervals declared as noisy during the respectively defined time period.

At block 720, the total time duration of noisy intervals is accumulated in one or more noise duration timers, each having different time resolutions. Each noise duration timer adds the length of the declared noisy interval to any accumulated noise duration to determine the total duration of noisy intervals declared over a respectively defined period of time. The noise duration timers may include a thirty second timer, a one day timer, and a total noise duration timer which accumulates the total duration of noisy intervals since the time of device implant or the most recent device interrogation session.

At block 725, a noisy interval counter value and/or the accumulated time in a noise duration timer, each corresponding to a relatively short period of time, are compared to a short-term high level noise condition. For example, a thirty-second noisy interval counter and/or a thirty-second noisy duration timer may be compared to a high-level noise condition. If a threshold number of noise intervals and/or a threshold total time of declared noisy intervals is reached, the high-level noise condition is met. Storage of the noisy episode is triggered causing the ECG signal to be stored at block 730. In other words, upon satisfying a high level noise condition over a short period of time, e.g. about two minutes or less, the ECG signal is stored for an interval of time, e.g. thirty seconds up to about two minutes, to allow a clinician or other user to evaluate the noise for troubleshooting purposes.

Alternatively, at block 725, the short-term high level noise condition may be dynamically defined based on a "noisiest" interval sensed since device implant or last device interrogation. Upon declaring a new noisy interval, the noisy interval duration and/or number of VR senses and over range flags causing the new noisy interval declaration are compared to a previously stored noisy interval. If the new noisy interval is longer and/or has a greater number of noise signals than the stored noisy interval, the new noisy interval is stored in the device memory as the "noisiest" interval. Thus, in this embodiment, the short-term "noise burden" measured at block 725 is the duration and/or number of noise signals occurring in a single noisy interval, and the short-term high level noise condition is dynamically defined based on the noisiest interval stored in memory. In this way, the noisiest interval encountered since device implant or the last interrogation session is always stored in memory and available for review by a clinician.

At block 735, a relatively longer-term noisy interval counter and/or noise duration timer are compared to a noise threshold. In one embodiment, the total noisy interval count since the time of implant or last interrogation session and/or the total time duration of declared noisy intervals accumulated in a noise duration timer since the time of implant or last interrogation are compared to predefined threshold values. The threshold may be defined as an absolute number of noisy intervals or time value or as a percentage of the total intervals detected or time elapsed. For example, a noise threshold may be defined as 5% of all depolarization intervals being declared as noisy. If a noise threshold is met, a noise warning is generated at block 740 to alert the physician that corrective action may be required in order to ensure proper sensing and arrhythmia detection. Such action may include reprogramming sensing or detection parameters or repositioning an electrode or an implanted device. The warning along with other noise diagnostics determined in method 700 may be included in a data summary that is transmitted to an external device and on to a networked expert database. The data summary may correspond, for example, to a "quick look" summary as generally disclosed in U.S. Pat. No. 6,599,250 (Webb, et al.), hereby incorporated herein by reference in its entirety.

At block 745, noise trends may be generated based on the data accumulated by the noise interval counters and noise timers to provide a clinician with an overview of improving, worsening or stable noise conditions. For example, the trend in the number of noisy intervals declared and total noise interval time per day may be charted and presented in a graphical display for review by a clinician.

It will be apparent from the foregoing that while particular embodiments of the invention have been illustrated and described, various modifications can be made without departing from the scope of the invention as set forth in the following claims.

The invention claimed is:

1. An implantable medical device, comprising:
sensing circuitry for receiving a cardiac signal, sensing cardiac depolarization signals and measuring depolarization intervals occurring between the sensed cardiac depolarization signals;
an arrhythmia detection module for detecting arrhythmia events from the measured depolarization intervals; and
a noise detection module for sensing a noise signal in the cardiac electrical signal and declaring a depolarization interval defined by a first sensed cardiac depolarization signal and a next sensed cardiac depolarization signal as a noisy interval in response to the noise signal being sensed during the depolarization interval;
wherein the detection circuitry configured to inhibit detecting an arrhythmia event in response to the noisy depolarization interval.

2. The device of claim 1 wherein sensing the noise signal comprises sensing one or more signals exceeding a sensing threshold within a predetermined time interval of the first sensed cardiac depolarization signal.

3. The device of claim 2 further comprising threshold setting circuitry for setting the sensing threshold as an automatically adjusted threshold comprising a first threshold level and a second threshold level, the first and second threshold levels separated by a first linear decay rate and the second threshold level followed by a second linear decay rate different than the first linear decay rate.

4. The device of claim 1 wherein sensing the noise signal comprises sensing an over range signal.

5. The device of claim 4 wherein the sensing circuitry comprises an input amplifier and an analog-to-digital converter and the over range signal is a signal causing one of an input amplifier saturation, an analog-to-digital converter amplitude over range, and an analog-to-digital converter signal differential over range.

6. The device of claim 5 further comprising means for clearing the over range signal by shorting a differential feedback of the input amplifier to restore a zero input state of the input amplifier in response to the over range signal.

7. The device of claim 1 further comprising means for storing time markers of sensed signals and corresponding signal labels wherein the next sensed cardiac depolarization signal is assigned a unique label corresponding to a noisy interval.

8. The device of claim 1 wherein the arrhythmia detection module comprises an arrhythmia event interval counter that is incremented in response to a measured cardiac depolarization interval falling into a detection interval range, and wherein the arrhythmia detection module inhibits detecting an arrhythmia event by not incrementing the arrhythmia event interval counter in response to the noisy interval.

9. The device of claim 8 wherein the arrhythmia event interval counter corresponds to one of an arrhythmia onset detection interval counter and an arrhythmia termination detection interval counter.

10. The device of claim 8 wherein not incrementing the arrhythmia event interval counter comprises decrementing the arrhythmia event interval counter by a predetermined integer.

11. The device of claim 10 wherein decrementing the arrhythmia event interval counter comprises reclassifying a most recent cardiac depolarization interval falling into the detection interval range as a non-detection interval.

12. The device of claim 1 wherein the arrhythmia detection module comprises an arrhythmia detection timer and detecting an arrhythmia event comprises starting the arrhythmia detection timer in response to the first sensed cardiac depolarization signal, and wherein inhibiting detecting the arrhythmia event comprises restarting the arrhythmia detection timer upon the next sensed cardiac depolarization signal in response to the noisy interval.

13. The device of claim 12 wherein the arrhythmia detection module is configured to determine if the arrhythmia detection timer exceeds an arrhythmia event detection threshold in response to sensing the noise signal and detects the arrhythmia in response to the arrhythmia detection timer exceeding the detection threshold at the time of the sensed noise signal.

14. The device of claim 13 further comprising an arrhythmia duration timer and wherein the arrhythmia detection module restarts the arrhythmia duration timer upon a second next sensed cardiac depolarization signal occurring after the next sensed cardiac depolarization signal.

15. The device of claim 12 wherein the diagnostic module further configured to generate a trend in the noise burden and further comprising memory for storing cardiac signal data, wherein the diagnostic module is further configured to compare the noise burden to a trigger threshold and trigger storage of the monitored cardiac signal in the memory in response to the noise burden exceeding the trigger threshold.

16. The device of claim 12 wherein the diagnostic module further configured to determine a diagnostic metric corresponding to sensed cardiac depolarization signals and exclude the first and next sensed cardiac depolarization signals from the computing in response to the noisy interval.

17. The device of claim 1 further comprising a diagnostics module configured to determine a noise burden in response to the declared noisy interval.

18. The device of claim 17 wherein determining the noise burden comprises determining a total number of declared noisy intervals occurring over a predetermined time period.

19. The device of claim 17 wherein determining the noise burden comprises determining a total time duration of declared noisy intervals occurring over a predetermined time period.

20. The device of claim 17 wherein the diagnostics module further configured to compare the noise burden to a threshold and generate a warning in response to the noise burden exceeding the threshold.

21. A method for use in an implantable medical device, comprising:

monitoring a physiological signal for sensing physiological events and detecting a physiological condition in response to the sensed physiological events;

sensing a first event from the physiological signal;

sensing a noise signal in the physiological signal;

sensing a next event from the physiological signal wherein the first event and the next event define a signal interval;

declaring the signal interval as a noisy interval in response to the sensed noise signal occurring after the first event and prior to the next event; and inhibiting detecting the physiological condition in response to the declared noisy interval.

22. The method of claim 21 wherein sensing the noise signal comprises sensing one or more signals exceeding a sensing threshold within a predetermined time interval of the first event.

23. The method of claim 22 wherein the sensing threshold is an automatically adjusted sensing threshold comprising a first threshold level and a second threshold level, the first and second threshold levels separated by a first linear decay rate and the second threshold level followed by a second linear decay rate different than the first linear decay rate.

24. The method of claim 22 wherein sensing the noise signal comprises detecting an over range signal, and wherein the over range signal is a signal causing one of an input amplifier saturation, an analog-to-digital converter amplitude over range, and an analog-to-digital converter signal differential over range.

25. The method of claim 24 further comprising clearing the over range signal by shorting a differential feedback of the input amplifier to restore a zero input state of the input amplifier in response to the over range signal.

26. The method of claim 21 wherein detecting the physiological condition comprises measuring the interval between sensed first event and next event and incrementing a detection counter when the measured interval corresponds to a physiological condition detection interval, and wherein inhibiting detecting the physiological condition comprises not incrementing the detection counter in response to the signal interval being declared a noisy interval.

27. The method of claim 26 wherein the detection counter corresponds to one of an onset detection counter and a termination detection counter.

28. The method of claim 26 wherein not incrementing the detection counter comprises decrementing the detection counter.

* * * * *